(12) United States Patent
Xu et al.

(10) Patent No.: US 11,666,865 B2
(45) Date of Patent: Jun. 6, 2023

(54) METHOD OF MAKING CARBON MOLECULAR SIEVE MEMBRANES

(71) Applicants: Dow Global Technologies LLC, Midland, MI (US); Georgia Tech Research Corporation, Atlanta, GA (US)

(72) Inventors: Liren Xu, Spring, TX (US); Thomas Fitzgibbons, Lake Jackson, TX (US); Mark K. Brayden, Plaquemine, LA (US); Marcos V. Martinez, Freeport, TX (US); William J. Koros, Atlanta, GA (US); Wulin Qiu, Snellville, GA (US)

(73) Assignees: Dow Global Technologies LLC, Midland, MI (US); Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 17/051,571

(22) PCT Filed: Apr. 3, 2019

(86) PCT No.: PCT/US2019/022852
§ 371 (c)(1),
(2) Date: Oct. 29, 2020

(87) PCT Pub. No.: WO2019/212648
PCT Pub. Date: Nov. 7, 2019

(65) Prior Publication Data
US 2021/0129085 A1    May 6, 2021

Related U.S. Application Data

(60) Provisional application No. 62/818,170, filed on Mar. 14, 2019, provisional application No. 62/665,849, filed on May 2, 2018.

(51) Int. Cl.
| | |
|---|---|
| *B01D 67/00* | (2006.01) |
| *B01D 53/22* | (2006.01) |
| *B01D 69/02* | (2006.01) |
| *B01D 69/08* | (2006.01) |
| *B01D 71/02* | (2006.01) |
| *C07C 7/144* | (2006.01) |

(52) U.S. Cl.
CPC ....... *B01D 67/0067* (2013.01); *B01D 53/228* (2013.01); *B01D 69/02* (2013.01); *B01D 69/088* (2013.01); *B01D 71/021* (2013.01); *B01D 71/028* (2013.01); *C07C 7/144* (2013.01); *B01D 2053/224* (2013.01); *B01D 2323/08* (2013.01); *B01D 2325/022* (2013.01); *B01D 2325/20* (2013.01)

(58) Field of Classification Search
None
See application file for complete search history.

(56) References Cited

U.S. PATENT DOCUMENTS

| | | | |
|---|---|---|---|
| 5,288,304 A | 2/1994 | Koros et al. | |
| 5,912,048 A * | 6/1999 | Rao | B01D 71/021 427/228 |
| 6,299,669 B1 | 9/2001 | Koros et al. | |
| 6,565,631 B2 | 5/2003 | Koros et al. | |
| 7,947,114 B2 | 5/2011 | Hagg et al. | |
| 8,486,179 B2 | 7/2013 | Kiyono et al. | |
| 8,709,133 B2 | 4/2014 | Kiyono et al. | |
| 10,150,840 B2 | 12/2018 | Xu | |
| 10,441,925 B2 | 10/2019 | Weber et al. | |
| 2002/0033096 A1 | 3/2002 | Koros et al. | |
| 2013/0333562 A1 | 12/2013 | Koros et al. | |
| 2015/0182921 A1 | 7/2015 | Koros et al. | |

FOREIGN PATENT DOCUMENTS

| | | |
|---|---|---|
| CN | 101113207 A | 1/2008 |
| CN | 103237588 A | 8/2013 |
| CN | 104529462 A | 4/2015 |
| CN | 105621389 A | 6/2016 |
| EP | 0459623 A1 * 12/1991 | ............. B01D 71/02 |

(Continued)

OTHER PUBLICATIONS

Communication pursuant to Rules 161(1) and 162 EPC, dated Dec. 12, 2020, pertaining to European Patent Application No. 19725435.2.

International Search Report and Written Opinion pertaining to PCT/US2019/022852, dated Jul. 23, 2019.

Jones et al., "Carbon molecular-sieve gas separation membranes-II. Regeneration following organic exposure", Carbon., 1994, 32(8), 427-432.

Jones et al., "Characterization of ultrmicroporous carbon membranes with humidified feeds", Ind Eng Chem Res., 1995, 34(1), 58-63.

Jones et al., "Carbon composite membranes—a solution to adverse humidity effects", Ind Eng Chem Res., 1995, 34(1), 164-167.

(Continued)

*Primary Examiner* — Jason M Greene
(74) *Attorney, Agent, or Firm* — Dinsmore & Shohl LLP

(57) ABSTRACT

The invention is an improved method of making an improved carbon molecular sieve (CMS) membrane in which a precursor polymer (e.g., polyimide) is pyrolyzed at a pyrolysis temperature to form a CMS membrane that is cooled to ambient temperature (about 40° C. or 30° C. to about 20° C.). The CMS membrane is then reheated to a reheating temperature of at least 250° C. to 400° C. to form the improved CMS membrane. The CMS have a novel microstructure as determined by Raman spectroscopy. The improved CMS membranes have shown an improved combination of selectivity and permeance as well as stability for separating light hydrocarbon gas molecules such as $C_1$ to $C_6$ hydrocarbon gases (e.g., methane, ethane, propane, ethylene, propylene, butane, butylene).

16 Claims, No Drawings

(56) References Cited

FOREIGN PATENT DOCUMENTS

| EP | 459623 A1 | 12/1991 |
| JP | 60151317 A | 8/1985 |
| JP | 2005270817 A | 10/2005 |
| JP | 2014047344 A | 3/2014 |
| WO | 0053299 A1 | 9/2000 |
| WO | 2017105836 A1 | 6/2017 |

OTHER PUBLICATIONS

Kiyono et al., "Carbon molecular sieve membranes for natural gas separations", Georgia Institute of Technology, Ph. D., 2010 (p. 153-162).

Kusakabe et al., "Gas Permeation and Micropore Structure of Carbon Molecular Sieving Membranes Modified by Oxidation", Journal of Membrane Science, 1998, 59-67.

Koresh et al., "Molecular Sieve Carbon Permselective Membrane. Part I. Presentation of a New Device for Gas Mixture Separation" Separation Science and Technology, 1983, 18(8), 723-734.

Lagorsse et al., "Aging study of carbon molecular sieve membranes", J Membr Sci., 2008, 310, 494-502.

Menendez et al., "Aging of carbon membranes under different environments", Carbon, 2001, 39(5), 733-740.

Steel et al., "Investigation of Porosity of Carbon Materials and Related Effects on Gas Separation Properties", Carbon, 2003, 41, 253-266.

Suda et al., "Gas Permeation through Micropores of Carbon Molecular Sieve Membranes Derived from Kapton Polyimide", J. Phys. Chem. B, 1997, 101, 3988-3994.

Xu et al., "Physical Aging in Carbon Molecular Sieve Membranes", Carbon, 2014, 80, 155-166.

Cui et al., "Physical aging of 6FDA-based polyimide membranes monitored by gas permeability", Polymer, 2011, 52(15), 3374-80.

Fuertes, Antonio B., "Effect of Air on Gas Separation Properties of Adsorption-selective Carbon Membranes", Carbon, 32001, 9, 5, 697.

Geiszler et al., "Effects of Polyimide Pyrolysis Conditions on Carbon Molecular Sieve Membrane Properties", Industrial & Engineering Chemistry Research, 1996, 35, 2999-3003.

Huang et al., "Effect of temperature on physical aging of thin glassy polymer films", Macromolecules, 2005, 38(24):10148-54.

Huang et al., "Physical aging of thin glassy polymer films monitored by gas permeability", Polymer, 2004, 45 (25):8377-93.

Kiyono et al., "Generalization of Effect of Oxygen Exposure on Formation and Performance of Carbon Molecular Sieve Membranes", Carbon, 48, 2010, 4442-4449.

Kiyono et al., "Effect of Pyrolysis Atmosphere on Separation Performance of Carbon Molecular Sieve Membranes", Journal of Membrane Science, 359, 2010, 2-10.

Kiyono et al., "Effect of Polymer Precursors on Carbon Molecular Sieve Structure and Separation Performance Properties", Carbon, 48, 2010, 4432-4441.

Kim et al., "Effects of $CO_2$ exposure and physical aging on the gas permeability of thin 6FDA-based polyimide membranes—Part 2. with crosslinking", J Membr Sci., 2006, 282(1-2):32-43.

Kim et al., "Physical aging of thin 6FDA-based polyimide membranes containing carboxyl acid groups. Part I. Transport properties", Polymer, 2006, 47(9):3094-103.

Lin et al., "Gas permeability, diffusivity, solubility, and aging characteristics of 6FDA-durene polyimide membranes", J Membr Sci., 2001, 186(2):183-93.

Rowe et al., "Influence of previous history on physical aging in thin glassy polymer films as gas separation membranes". Polymer, 2010, 51(16):3784-92.

Rungta et al., "Carbon Molecular Sieve Dense Film Membranes Derived from Matrimid for Ethylene-ethane Separation", Carbon, 2012, 50, 2488-1502.

Wessling et al., "Time-dependent permeation of carbon-dioxide through a polyimide membrane above the plasticization pressure", J Appl Polym Sci, 1995, 58(11):1959-66.

Xu et al., "Matrimid Derived Carbon Molecular Sieve Hollow Fiber Membranes for Ethylene-ethane Separation", Journal of Membrane Science, 380, 2011, 138-147.

International Search Report and Written Opinion pertaining to PCT/US2019/022848, dated Sep. 24, 2019.

Chinese Search Report, dated Mar. 11, 2022 pertaining to Chinese Patent Application No. 201980024944.3 4 pages.

Chinese Office Action, dated Mar. 21, 2022, pertaining to Chinese Patent Application No. 201980024944.3 4 pages.

Chinese Office Action, dated Mar. 30, 2022, pertaining to Chinese Patent Application 201980025184.8 5 pages.

Chinese Search Report, dated Mar. 24, 2022, pertaining to Chinese Patent Application 201980025184.8 3 pages.

GCC Examination Report pertaining to GCC Application No. GC2019-37247 dated May 18, 2021 4 pages.

Notice of Allowance pertaining to U.S. Appl. No. 17/051,620 dated Apr. 27, 2022 9 pages.

Non-Final Office Action pertaining to U.S. Appl. No. 17/051,620 dated Jan. 3, 2022 21 pages.

Communication pursuant to Article 94(3)EPC, dated Dec. 8, 2022 pertaining to European Patent Application No. 19725435.2 6 pages.

Chinese second Office Action, dated Oct. 8, 2022, pertaining to Chinese Patent Application No. 201980025184.8 6 pages.

* cited by examiner

METHOD OF MAKING CARBON MOLECULAR SIEVE MEMBRANES

FIELD OF THE INVENTION

The invention relates to carbon molecular sieve (CMS) membranes for use in gas separation. In particular the invention relates to a method for producing CMS membranes with improved selectivity, permeability and stability particularly for smaller gas molecules such as hydrogen.

BACKGROUND OF THE INVENTION

Membranes are widely used for the separation of gases and liquids, including for example, separating acid gases, such as $CO_2$ and $H_2S$ from natural gas, and the removal of $O_2$ from air. Gas transport through such membranes is commonly modeled by the sorption-diffusion mechanism. Currently, polymeric membranes are well studied and widely available for gaseous separations due to easy process-ability and low cost. CMS membranes, however, have been shown to have attractive separation performance properties exceeding that of polymeric membranes.

CMS membranes are typically produced through thermal pyrolysis of polymer precursors. For example, it is known that defect-free hollow fiber CMS membranes can be produced by pyrolyzing cellulose hollow fibers (J. E. Koresh and A. Soffer, Molecular sieve permselective membrane. Part I. Presentation of a new device for gas mixture separation. Separation Science and Technology, 18, 8 (1983)). In addition, many other polymers have been used to produce CMS membranes in fiber and dense film form, among which polyimides have been favored. Polyimides have a high glass transition temperature, are easy to process, and have one of the highest separation performance properties among other polymeric membranes, even prior to pyrolysis.

U.S. Pat. No. 6,565,631 to Koros et al., which is incorporated herein by reference, describes a method of synthesizing CMS membranes. In particular, a polyimide hollow fiber was placed in a pyrolysis furnace with an evacuated environment, with a pyrolysis pressure of between 0.01 and 0.10 mm Hg air. U.S. Pat. No. 6,565,631 also discloses a method of using CMS membranes to separate $CO_2$ from a methane stream containing 10% $CO_2$, at 1000 psia and 50° C., with a selectivity of approximately 45, a selectivity that is much higher than typical commercial polymeric membranes. Other patents that describe processes for producing carbon membranes (both asymmetric hollow "filamentary" and flat sheets), and applications for gas separation, include U.S. Pat. No. 5,288,304, and EP Patent No. 0459623, which are incorporated herein in their entireties.

Prior research has shown that CMS membrane separation properties are primarily affected by the following factors: (1) pyrolysis precursor, (2) pyrolysis temperature, (3) thermal soak time, and (4) pyrolysis atmosphere. For example, Steel and Koros performed a detailed investigation of the impact of pyrolysis temperature, thermal soak time, and polymer composition on the performance of carbon membranes. (K. M. Steel and W. J. Koros, Investigation of Porosity of Carbon Materials and Related Effects on Gas Separation Properties, Carbon, 41, 253 (2003).) Membranes were produced in an air atmosphere at 0.05 mm Hg pressure. The results showed that increases in both temperature and thermal soak time increased the selectivity but decreased permeance for $CO_2/CH_4$ separation. In addition, Steel et al showed that a precursor polymer with a rigid, tightly packed structure tends to lead to a CMS membrane having higher selectivity compared with less rigid precursor polymers.

The impact of pyrolysis atmosphere has been researched only to a limited extent. Suda and Haraya disclosed the formation of CMS membranes under different environments. (H. Suda and K. Haraya, Gas Permeation Through Micropores of Carbon Molecular Sieve Membranes Derived From Kapton Polyimide, J. Phys. Chem. B, 101, 3988 (1997).) CMS dense films were prepared from polyimide KAPTON at 1000° C. in either argon or in vacuum. According to their gas separation properties, the results of an 02/N2 separation were almost the same between 6 membranes formed under the different atmospheres. Suda and Haraya did not disclose the effects of atmosphere on $CO_2$ separation from natural gas, nor disclose how separation properties vary with ability and low cost. Similarly, Geiszler and Koros disclosed the results of CMS fibers produced from pyrolysis of fluorinated polyimide in helium and argon for both $O_2/N_2$ and $H_2/N_2$ separations (V. C. Geiszler and W. J. Koros, Effects of Polyimide Pyrolysis Atmosphere on Separation Performance of Carbon Molecular Sieve Membranes, *Ind. Eng. Chem. Res.* 1996, 35, 2999-3003). That paper disclosed a slightly higher selectivity with vacuum pyrolysis than the purged pyrolysis processes. In addition, Geiszler and Koros showed that the flow rate of the purge gases impacted performance Geiszler and Koros, however, did not disclose the effects of atmosphere on $CO_2$ separation from natural gas, or the effects of oxygen concentration on separation properties. None of the aforementioned describe the long term use of the CMS membranes and the stability of the membranes to maintain the permeance and selectivity for particular gas molecules of interest. The aforementioned also fail to describe methods of optimizing and improving the selectivity and permeance for a desired retentate gas molecule such as hydrogen with improved stability of the same.

More recently, CMS membranes have been discovered to undergo substantial aging that deleteriously affects the performance as described by Liren Xu, et al., *Physical Aging in Carbon Molecular Sieve Membranes, Carbon,* 80 (2014) 155-166. For example, the permeance of a desired gas retentate molecule may be reduced by a factor of 2 to 4 within 5 days of cooling to room temperature with only a very small increase in selectivity (e.g., 10% or so). WO2017105836 has described CMS membranes being treated to improve the permeance of olefins from paraffins by exposing the CMS membranes shortly after pyrolysis to a light olefin such as propylene at a temperature of 35° C.

It would be desirable to provide a method to make a CMS membrane and CMS membrane made by the method that addresses one or more of the problems of the prior art such as one described above such as improving the selectivity for select gases such as light hydrocarbons while achieving useful permeances. It would also be desirable to have such CMS membrane maintain the same selectivity and permeance whether being stored for use or while being used (i.e., stable) and that could be quickly regenerated after being used.

SUMMARY OF THE INVENTION

A first aspect of the invention is a method of making a carbon molecular sieve membrane comprising, (i) providing a precursor polymer;
(ii) heating said precursor polymer to a pyrolysis temperature where the precursor polymer undergoes pyrolysis to form the carbon molecular sieve membrane;
(iii) cooling the carbon molecular sieve membrane to a cooling temperature less than or equal to 50° C.; and
(iv) after the cooling, heating the carbon molecular sieve membrane to a reheating temperature of at least 250° C. to at most 400° C. for a reheating time from 15 minutes to 48 hours under a reheating atmosphere and then
(v) cooling back to below 50° C.

The method of the invention may realize a CMS that has an improved combination of selectivity and permeance particularly for the separation of light hydrocarbons such as from methane, or streams from natural gas steam methane reformers, or light hydrocarbon streams such as found in olefin cracker gas streams or propane dehydrogenation unit streams. In addition it has been discovered that the method may improve the stability of the CMS membrane (i.e., substantially retains the permeance and selectivity over time during use), wherein the underlying microstructure has been fundamentally altered.

A second aspect of the invention is a carbon molecular sieve (CMS) membrane comprising a carbon membrane having a Raman G and D peak, wherein the G peak has a wavenumber of at least 1588 cm$^{-1}$ and an intensity of ratio of D to G peak of at most 1.12 as determined at a Raman excitation wavelength of 532 nm. The carbon membrane may be any structure have a thin wall wherein a gas may be passed through the wall and one gas is preferentially passed through compared to another gas molecule in a gas feed such as an olefin and its corresponding paraffin.

A third aspect of the invention is a method for separating gases in a gas feed having a plurality of smaller gas molecules and a plurality of larger gas molecules comprising
(i) providing the carbon molecular sieve membrane of the second aspect; and
(ii) flowing the gas feed through said carbon molecular sieve membrane to produce a first stream having an increased concentration of the smaller gas molecules and as second stream having an increased concentration of the larger gas molecules.

The gas separation method is particularly useful for separating gases in gas streams such as those arising from natural gas steam methane reformers, or light hydrocarbon gas streams arising from olefin crackers. In particular they are useful in separating gases in gas feed comprising at least two of the following: ethylene, ethane, propylene, propane, methane, butane or butylene. Preferably the gas feed comprising at least two of least two of the following: ethylene, ethane, propylene, propane, methane, butane or butylene.

DETAILED DESCRIPTION OF THE INVENTION

The precursor polymer may be any useful polymer for making CMS membranes, with polyimides generally being suitable. The polyimide may be a conventional or fluorinated polyimide. Desirable polyimides typically contain at least two different moieties selected from 2,4,6-trimethyl-1,3-phenylene diamine (DAM), oxydianaline (ODA), dimethyl-3,7-diaminodiphenyl-thiophene-5,5'-dioxide (DDBT), 3,5-diaminobenzoic acide (DABA), 2.3,5,6-tetramethyl-1,4-phenylene diamine (durene), meta-phenylenediamine (m-PDA), 2,4-diaminotolune (2,4-DAT), tetramethylmethylenedianaline (TMMDA), 4,4'-diamino 2,2'-biphenyl disulfonic acid (BDSA); 5,5'-[2,2,2-trifluoro-1-(trifluoromethyl)ethylidene]-1,3-isobenzofurandion (6FDA), 3,3',4,4'-biphenyl tetracarboxylic dianhydride (BPDA), pyromellitic dianhydride (PMDA), 1,4,5,8-naphthalene tetracarboxylic dianhydride (NTDA), and benzophenone tetracarboxylic dianhydride (BTDA), with two or more of 6FDA, BPDA and DAM being preferred.

A particularly useful polyimide, designated as 61-DA/BPDA-DAM, may be synthesized via thermal or chemical processes from a combination of three monomers: DAM; 6FDA, and BPDA, each commercially available for example from Sigma-Aldrich Corporation. Formula 1 below shows a representative structure for 6FDA/BPDA-DAM, with a potential for adjusting the ratio between X and Y to tune polymer properties. As used in examples below, a 1:1 ratio of component X and component Y may also abbreviated as 6FDA/BPDA(1:1)-DAM.

Formula 1

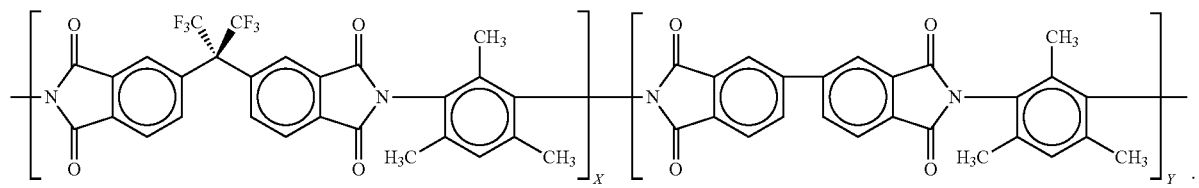

Chemical structure of 6FDA/BPDA-DAM

A second particularly useful polyimide, designated as 6FDA-DAM lacks BPDA such that Y equals zero in Formula 1 above. Formula 2 below shows a representative structure for this polyimide.

Formula 2

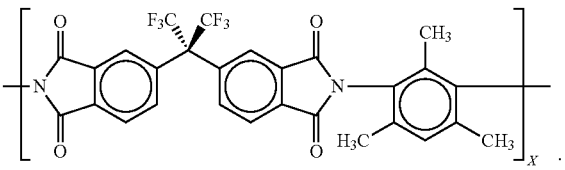

Chemical structure of 6FDA-DAM

A third useful polyimide is MATRIMID™ 5218 (Huntsman Advanced Materials), a commercially available polyimide that is a copolymer of 3,3',4,4'-benzo-phenonetetracarboxylic acid dianhydride and 5(6)-amino-1-(4'-aminophenyl)-1,3,3-trimethylindane (BTDA-DAPI).

Preferred polymeric precursor hollow fiber membranes, the hollow fibers as produced but not pyrolyzed, are substantially defect-free. "Defect-free" means that selectivity of a gas pair, typically oxygen ($O_2$) and nitrogen ($N_2$), through a hollow fiber membrane is at least 90 percent of the selectivity for the same gas pair through a dense film prepared from the same composition as that used to make the polymeric precursor hollow fiber membrane. By way of illustration, a 6FDA/BPDA(1:1)-DAM polymer has an intrinsic $O_2/N_2$ selectivity (also known as "dense film selectivity") of 4.1.

The precursor polymers are typically formed into hollow fibers or films. Conventional procedures to make these may be used. For example, coextrusion procedures including such as a dry-jet wet spinning process (in which an air gap exists between the tip of the spinneret and the coagulation or quench bath) or a wet spinning process (with zero air-gap distance) may be used to make the asymmetric hollow fibers.

Pyrolysis conditions influence carbon membrane physical properties and, accordingly, are chosen with care. Any suitable supporting means for holding the CMS membranes may be used during the pyrolysis including sandwiching between two metallic wire meshes or using a stainless steel mesh plate in combination with stainless steel wires and as described by U.S. Pat. No. 8,709,133 at col. 6 line 58 to col. 7, line 4, which is incorporated by reference.

Precursor polymers may be pyrolyzed to form the CMS membranes (i.e., carbonize the precursor polymer) under various inert gas purge or vacuum conditions, preferably under inert gas purge conditions, for the vacuum pyrolysis, preferably at low pressures (e.g. less than 0.1 millibar). U.S. Pat. No. 6,565,631 describes a heating method for pyrolysis of polymeric fibers to form CMS membranes, and is incorporated herein by reference. For either polymeric films or fibers, a pyrolysis temperature of between about 450° C. to about 800° C. may advantageously be used. The pyrolysis temperature may be adjusted in combination with the pyrolysis atmosphere to tune the performance properties of the resulting CMS membrane. For example, the pyrolysis temperature may be 1000° C. or more. Optionally, the pyrolysis temperature may be between about 500° C. and about 550° C. The pyrolysis soak time (i.e., the duration of time at the pyrolysis temperature) may vary (and may include no soak time) but advantageously is between about 1 hour to about 10 hours, alternatively from about 2 hours to about 8 hours, alternatively from about 4 hours to about 6 hours. An exemplary heating protocol may include starting at a first set point of about 50° C., then heating to a second set point of about 250° C. at a rate of about 13.3° C. per minute, then heating to a third set point of about 535° C. at a rate of about 3.85° C. per minute, and then a fourth set point of about 550° C. to 700° C. at a rate of about 0.25° C. per minute. The fourth set point is then optionally maintained for the determined soak time. After the heating cycle is complete, the system is typically allowed to cool while still under vacuum or in a controlled atmosphere.

Precursor polymers may be carbonized under various inert gas purge or vacuum conditions, preferably under inert gas purge conditions, for the vacuum pyrolysis, preferably at low pressures (e.g. less than 0.1 millibar). In one embodiment the pyrolysis utilizes a controlled purge gas atmosphere during pyrolysis in which low levels of oxygen are present in an inert gas. By way of example, an inert gas such as argon is used as the purge gas atmosphere. Other suitable inert gases include, but are not limited to, nitrogen, helium, or any combinations thereof. By using any suitable method such as a valve, the inert gas containing a specific concentration of oxygen may be introduced into the pyrolysis atmosphere. For example, the amount of oxygen in the purge atmosphere may be less than about 50 ppm (parts per million) $O_2$/Ar. Alternatively, the amount of oxygen in the purge atmosphere may be less than 40 ppm $O_2$/Ar. Embodiments include pyrolysis atmospheres with about 8 ppm, 7 ppm, or 4 ppm $O_2$/Ar.

After pyrolyzing, the CMS membrane that has formed is cooled to temperature around ambient such as below 50° C. The cooling may be at any useful rate, such as passively cooling (e.g., turning off the power to furnace and allowing to cool naturally). Alternatively, it may be desirable to more rapidly cool such as using known techniques to realize faster cooling such as cooling fans or employment of water cooled jackets or opening the furnace to the surrounding environment.

After cooling, the carbon molecular sieve membrane is reheated to a temperature from 250° C. to 400° C. (reheating temperature). Temperatures less than 250° C. fail to alter the microstructure of the disordered carbon structures to make the CMS membrane as discovered herein. These new CMS membranes having differing microstructures may be particularly useful for gas separations such as light hydrocarbon gas separation, including, for example, olefin/paraffin separations due to greater permeances compared to CMS membranes not having these microstructures. Desirably, the reheating temperature is at least about 275° C. to at most about 350° C. or 325° C.

The reheating time is generally from 15 minutes to 48 hours, with the time being dependent on the temperature, and may be any sufficient to realize the improved CMS membrane characteristics and microstructure desired such as further described below and may vary depending on the particular CMS membrane (e.g., type of precursor polymer and particular pyrolysis conditions). Generally, the amount of time is from several hours to several days or even a week. Typically, the time is from about 10 minutes, 30 minutes or 1 hour to 5 hours.

The time between the cooling until reheating may be any suitable time and may be several minutes to several days or weeks or longer. Illustratively, the reheating may occur within 5 days of cooling to ambient temperature. Even though the exposing may occur within 5 days, it may be desirable to expose the CMS membrane in as short as possible a time after cooling from pyrolysis such as within 4 days, 2 days, 1 day, 12 hours, 6 hours or even 1 hour. The CMS membranes when being reheated do not need to be fabricated into a separation module (apparatus capable of flowing gas through the CMS membrane), but may be reheated upon cooling in the same chamber of the furnace used to make the CMS membrane.

The atmosphere, during the reheating ("reheating atmosphere), may be static, flowing or combination thereof. Desirably, the atmosphere is static at least a portion of the time during the exposing and preferably is static the entire time of the exposing. Generally, the gas may be any including dry or wet air, inert gas (e.g., noble gas), nitrogen or vacuum. In an embodiment, at least a portion of the gas within the conditioning atmosphere flows through the CMS membrane walls. The atmosphere desirably is air, nitrogen or argon with air being preferred.

The pressure of the reheating atmosphere may be any useful and may range from a pressure below atmospheric pressure (vacuum) to several hundred pounds per square inch (psi). Desirably, the pressure is from atmospheric pressure to about 10 to 200 psi above atmospheric pressure. The pressure may also be varied during the exposing. When reheating the CMS membrane, where at least a portion of the gas in the atmosphere flows through the walls of the CMS membrane, the pressure differential across the wall may be any useful such as several psi to several hundred psi. Desirably, the pressure differential is from about 1, 5 or 10 to 25, 50 or 100 psi.

The gas permeation properties of a membrane can be determined by gas permeation experiments. Two intrinsic properties have utility in evaluating separation performance of a membrane material: its "permeability," a measure of the membrane's intrinsic productivity; and its "selectivity," a measure of the membrane's separation efficiency. One typically determines "permeability" in Barrer (1 Barrer=$10^{-10}$ [$cm^3$ (STP) cm]/[$cm^2$ s cmHg], calculated as the flux ($n_i$) divided by the partial pressure difference between the membrane upstream and downstream ($\Delta p_i$), and multiplied by the thickness of the membrane (l).

$$P_i = \frac{n_i l}{\Delta p_i}$$

Another term, "permeance," is defined herein as productivity of asymmetric hollow fiber membranes and is typically measured in Gas Permeation Units (GPU) (1 GPU=$10^{-6}$ [$cm^3$ (STP)]/[$cm^2$ s cmHg]), determined by dividing permeability by effective membrane separation layer thickness.

$$\left(\frac{P_i}{l}\right) = \frac{n_i}{\Delta p_i}$$

Finally, "selectivity" is defined herein as the ability of one gas's permeability through the membrane or permeance relative to the same property of another gas. It is measured as a unitless ratio.

$$\alpha_{i/j} = \frac{P_i}{P_j} = \frac{(P_i/l)}{(P_j/l)}$$

In a particular embodiment, the CMS membrane produced by the method enables a CMS membrane that has a permeance of at least 30 and preferably at least 100, 200 or even 250 GPU for hydrogen (permeate) and a selectivity of at least about 40 and preferably at least 100 or even 200 and a stability such that said permeance and selectivity varies less than 20% after being continuously separating a feed gas comprised of hydrogen gas molecule for 10 days. Desirably, the permeance and selectivity varies less than 15%, 10% or 5% after being continuously separating a feed gas comprised of a retentate and permeate gas molecule pair for 10, 30 or 60 days. In particular embodiments permeate is hydrogen and the other gas molecules gas molecule is comprised of at least one of ethylene, ethane, propylene, propane, butylene, butane, methane, carbon dioxide, oxygen, nitrogen, and hydrogen sulfide. Illustratively, the feed gas generally is comprised of at least 5% the permeate gas molecule (e.g., ethylene) with the remainder being one of the aforementioned gases or mixture of two or more of said gases. It is understood that when referring to retentate gas molecule, this refers the gas molecule that has a lower permeability or, in other words, slowly permeates through the membrane. Likewise, permeate refers to the gas molecule that has a higher permeability through the membrane or, in other words, permeates faster through the membrane.

The CMS membranes are particularly suitable for separating light hydrocarbons by flowing a gas feed containing, for example any one of the following olefins and their corresponding paraffin, ethylene, propylene, or butylene through the CMS membrane. The flowing results in a first stream have an increased concentration of the olefin and second stream having an increased concentration of the paraffin. The process may be utilized to separate an olefin from a. Likewise, the process exhibits the same stability as it relates to permeance and selectivity over time as described above. When practicing the process, the CMS membrane is desirably fabricated into a module comprising a sealable enclosure comprised of a plurality of carbon molecular sieve membranes that is comprised of at least one carbon molecular sieve membrane produced by the method of the invention that are contained within the sealable enclosure. The sealable enclosure having an inlet for introducing a gas feed comprised of at least two differing gas molecules; a first outlet for permitting egress of a permeate gas stream; and a second outlet for egress of a retentate gas stream.

The CMS membranes that are formed desirably are in the form of sheets or hollow fibers with asymmetric structures (asymmetric membranes). The membrane is desirably an asymmetric hollow fiber or sheet. Illustratively, the asymmetric hollow fiber has a wall that is defined by an inner surface and outer surface of said fiber and the wall has an inner porous support region (support layer) extending from the inner surface to an outer microporous region (separation layer) that extends from the inner porous support region to the outer surface. The outer microporous separation layer may be is desirably thin in absence. The separation layer is typically 10, 8.75, 7.5, 6.25, 5.5, 4.25 or 3.0 micrometers or less.

Typically, the outer separation layer of the hollow fiber has a thickness of at most 10% of the wall extending from the inner surface to the outer surface. The outer separation layer typically has a thickness of 0.05 micrometers to 10 micrometers, desirably 0.05 micrometers to 5 micrometers, more desirably 0.05 to 3 micrometer. Herein, microporous shall mean pores <2 nm in diameter; mesoporous shall mean 2-50 nm in diameter and macroporous shall mean >50 nm in diameter. The microstructure of the separation layer in CMS is generally characterized with microporous pores. The support layer is generally characterized by a microstructure where the pores are microporous, macroporous or both.

EXAMPLES

CMS Membrane Preparation:

The CMS membranes were made using 6FDA:BPDA-DAM polymer. The 6FDA:BPDA-DAM was acquired from Akron Polymer Systems, Akron, Ohio. The polymer was dried under vacuum at 110° C. for 24 hours and then a dope was formed. The dope was made by mixing the 6FDA:BPDA-DAM polymer with solvents and compounds in Table 1 and roll mixed in a Qorpak™ glass bottle sealed with a polytetrafluoroethylene (TEFLON™) cap and a rolling speed of 5 revolutions per minute (rpm) for a period of about 3 weeks to form a homogeneous dope.

TABLE 1

Dope formulation
Dope Composition

| Component | mass (gm) | weight % |
|---|---|---|
| 6FDA:BPDA-DAM | 60.0 | 20.0 |
| NMP | 142.7 | 47.5 |
| THF | 30.0 | 10.0 |
| Ethanol | 48.0 | 16.0 |
| LiNO$_3$ | 19.5 | 6.5 |

NMP = N-Methyl-2-pyrrolidone;
THF = Tetrahydrofuran

The homogeneous dope was loaded into a 500 milliliter (mL) syringe pump and allow the dope to degas overnight by heating the pump to a set point temperature of 50 C to 60 C using a heating tape.

Bore fluid (85 wt % NMP and 15 wt % water, based on total bore fluid weight) was loaded into a separate 100 mL syringe pump and then the dope and bore fluid were co-extruded through a spinneret operating at a flow rate for of 180 milliliters per hour (mL/hr) for the dope; 60 mL/hr bore fluid, filtering both the bore fluid and the dope in line between delivery pumps and the spinneret using 40 µm and 2 µm metal filters. The temperature was controlled using thermocouples and heating tape placed on the spinneret, dope filters and dope pump at a set point temperature of 70° C.

After passing through a fifteen centimeter (cm) air gap, the nascent fibers that were formed by the spinneret were quenched in a water bath (50° C.) and the fibers were allowed to phase separate. The fibers were collected using a 0.32 meter (M) diameter polyethylene drum passing over TEFLON guides and operating at a take-up rate of 30 meters per minute (M/min).

The fibers were cut from the drum and rinsed at least four times in separate water baths over a span of 48 hours. The rinsed fibers in glass containers and effect solvent exchange three times with methanol for 20 minutes and then hexane for 20 minutes before recovering the fibers and drying them under vacuum at a set point temperature of 110° C. for one hour or drying under vacuum at 75° C. for 3 hours.

Prior to pyrolyzing the fibers, a sample quantity of the above fibers (also known as "precursor fibers") were tested for skin integrity. One or more hollow precursor fibers were potted into a ¼ inch (0.64 cm) (outside diameter, OD) stainless steel tubing. Each tubing end was connected to a ¼ inch (0.64 cm) stainless steel tee; and each tee was connected to ¼ inch (0.64 cm) female and male NPT tube adapters, which were sealed to NPT connections with epoxy. Pure gas permeation tests were performed in a constant-volume system maintained at 35° C. For each permeation test, the entire system and leak rate was determined to ensure that the leakage was less than 1 percent of the permeation rate of the slowest gas. After evacuating, the upstream end was pressurized (end closest to feed source) of the tube with feed gas (e.g. pure oxygen or pure nitrogen) while keeping the downstream end (end furthest from feed source) under vacuum. The pressure rise was recorded in a constant, known downstream volume over time using LAB VIEW software (National Instruments, Austin, Tex.) until reaching steady state. The permeance of each gas was determined through the membrane by the rate of pressure rise, the membrane area and the pressure difference across the membrane. The selectivity of each gas pair as a ratio of the individual gas permeance was calculated.

The hollow fibers were pyrolyzed to form the CMS membranes by placing the precursor fibers on a stainless steel wire mesh plate each of them bound separately to the plate using stainless steel wire. The combination of hollow fibers and mesh plate were placed into a quartz tube that sits in a tube furnace. The fibers were pyrolyzed under an inert gas (argon flowing at a rate of 200 standard cubic centimeters per minute (sccm)). Prior to pyrolyzing the furnace was purged of oxygen by evacuating and then purging the tube furnace for a minimum of four hours to reduce the oxygen level to less than 1 ppm. All of the fibers were heated at a ramp rate of 10° C./minute up to 250° C., then heated at 3° C./min to 660° C. and finally heated at 0.25° C./min to 675° C. and held at that temperature for 2 hours (soak time). After the soak time, the furnace was shut off, cooled under the flowing argon (passively cooled), which typically cooled in about 8 to 10 hours.

For reheating below 200° C., the newly formed cooled CMS fibers were removed from the pyrolysis furnace, placed upon an aluminum foil and placed into a preheated convection oven at the desired reheating temperature, the atmosphere being atmospheric air. For reheating to above 200° C. the fibers were left in the quartz tube of the pyrolysis furnace, but upon cooling to room temperature, the tube was removed from the furnace and the furnace reheated to the desired reheating temperature. The sealed end plates were removed from the quartz tube and the tube was placed back in the pyrolysis furnace for the desired time, with the atmosphere being ambient air. After the reheating, the CMS hollow fiber membranes were removed from the furnace and potted into modules as described above. The modules were allowed to set over night (e.g., about 12 to 16 hours) before being loaded into the permeation testing system.

The permeation tests were determined using pure gases, for example, hydrogen and ethylene as 50 psia upstream and downstream vacuum at 35° C. using the constant volume method, similar to the precursor fiber testing. For the hydrogen tests, the system was evacuated and then hydrogen was fed on the shell side while downstream was kept under vacuum for ~4 h to ensure a steady state was obtained before data recording. For ethylene tests, ethylene was fed and maintained overnight before data recording. The tests were typically repeated 2-4 times. The average rate of pressure rise was then used to calculate permeance of gas through the hollow fibers, and selectivity was calculated as the ratio of the permeances of hydrogen and ethylene. The results of the tests are shown in Table 2.

From the results shown in Table 2, it is readily apparent that the Comparative Examples without any reheating and employing reheating outside of the claimed range had fundamentally different separation behavior.

Further Examples were performed in a similar fashion as described above as well as determining the permeance for propylene and propane tested in a similar manner as described above. In addition, the microstructure of one of Examples and two of the Comparative Examples were determined using Raman spectroscopy as described below. The results for the permeance for these Examples and Comparative Examples is shown in Table 3 and the Raman results are shown in Table 4.

Raman spectroscopy was performed on carbon membrane hollow fibers in a side-on geometry with a ThermoScientific DXR MicroRaman spectrometer in a 180 degree backscatter geometry. A 20× microscope objective with a 0.3 NA (numerical aperture) was utilized with a 532 nm excitation source. A CCD detector was used to collect the data. The microRaman system was interfaced with a computer system that controlled both the high resolution grating, and the laser power was controlled via neutral density filters through the OMNIC software package. Peak fitting was performed using two Lorentzian peaks and a linear background using the multipeak fitting algorithm within IgorPro. The I(D)/I(G) ratio is the ratio of the D peak and G peak amplitudes.

From the results in Tables 3 and 4, it is readily apparent that a fundamentally different microstructure was realized for the CMS membranes subjected to the reheating of the invention. This is also clearly displayed by the differing permeances of differing gases compared to the comparative examples. They also show the improved performance of the CMS membranes of the present invention for use in separating light hydrocarbon gases such as propylene from propane.

TABLE 2

| Example | Reheating Temperature(° C.) | Reheating time (hour) | $H_2$ Permeance (GPU) | $\alpha_{H_2/C_2H_4}$ |
|---|---|---|---|---|
| Comp. 1 | None | | 193 ± 60 | 24 ± 10 |
| Comp. 2 | 60 | 25 | 245 ± 38 | 39.6 ± 1.8 |
| Comp. 3 | 60 | 500 | 34.6 ± 2.5 | 194 ± 15.1 |
| Comp. 4 | 90 | 18 | 136.2 ± 30 | 112.7 ± 19.1 |
| Comp. 5 | 90 | 25 | 140.8 ± 33.2 | 131.9 ± 6.9 |
| Comp. 6 | 110 | 5 | 133.6 ± 9.2 | 134.5 ± 18.5 |
| Comp. 7 | 110 | 18 | 98.9 ± 26 | 290 ± 51.8 |
| Comp. 8 | 110 | 25 | 68.5 ± 0.3 | 335 ± 91.9 |
| Comp. 9 | 130 | 5 | 119.6 ± 21.1 | 197.1 ± 17.2 |
| Comp. 10 | 130 | 18 | 75 ± 10.4 | 344.2 ± 31.3 |
| Comp. 11 | 200 | 1 | 140 ± 26.8 | 318.3 ± 11.2 |
| Ex. 1 | 250 | 1 | 158 ± 39 | 2 ± 0.2 |
| Ex. 2 | 300 | 1 | 217.5 ± 21.8 | 4.2 ± 0.3 |

TABLE 3

| Example | Reheating Temperature (° C.) | Reheating time | Propylene Permeance (GPU) | $\alpha_{propylene/propane}$ |
|---|---|---|---|---|
| Comp. 12 | None | | 19.8 ± 0.3 | 22.6 ± 10 |
| Comp. 13 | 110 | 18 hours | 0.19 ± 0.07 | 60.6 ± 0.05 |
| Ex. 3* | 300 | 60 min | 70.5 | 7.2 |
| Ex. 4* | 300 | 30 min | 31.6 | 7.0 |
| Ex. 5* | 300 | 20 min | 8.1 | 13.3 |
| Ex. 6 | 280 | 45 min | 12.5 ± 1.3 | 20.6 ± 2.0 |
| Ex. 7 | 280 | 30 min | 25.8 ± 1.4 | 9.7 ± 2.0 |
| Ex. 8 | 280 | 20 min | 24.9 ± 0.3 | 10.7 ± 0.2 |
| Ex. 9* | 250 | 30 min | 6.2 | 45.4 |

*permeance test only run once.

TABLE 4

| Example | Raman G peak (cm-1) | I(D)/I(G) |
|---|---|---|
| Comp. 12 | 1586.2 ± 0.5 | 1.13 ± 0.01 |
| Comp. 13 | 1585.2± | 1.14 ± 0.03 |
| Ex. 3 | 1591.1± | 1.09 ± 0.01 |

What is claimed is:

1. A method of making a carbon molecular sieve membrane comprising,
   (i) providing a precursor polymer;
   (ii) heating said precursor polymer to a pyrolysis temperature where one or more gases surrounding the precursor polymer reach the pyrolysis temperature and the precursor polymer undergoes pyrolysis to form the carbon molecular sieve membrane;
   (iii) directly after heating the precursor polymer to form the carbon molecular sieve membrane, cooling the carbon molecular sieve membrane to a cooling temperature less than or equal to 50° C. by lowering the temperature of the one or more gases to the cooling temperature; and
   (iv) after the cooling, heating the carbon molecular sieve membrane to a reheating temperature of at least 250° C. to at most 400° C. for a reheating time from 15 minutes to 48 hours under a reheating atmosphere and then
   (v) cooling back to below 50° C.

2. The method of claim 1, wherein the reheating temperature is from 275° C. to 350° C.

3. The method of claim 1, wherein the reheating time is 30 minutes to 2 hours.

4. The method of claim 1, wherein the cooling temperature is from 20 to 30° C.

5. The method of claim 1, wherein the reheating atmosphere is an inert gas, nitrogen, air or mixture thereof.

6. The method of claim 1, wherein the precursor polymer is a polyimide.

7. A carbon molecular sieve membrane comprising a carbon membrane having a Raman G and D peak, wherein the G peak has a wavenumber of at least 1588cm$^{-1}$ and an intensity ratio of the D to the G peak of at most 1.12 as determined at a Raman excitation wavelength of 532 nm.

8. The carbon molecular sieve membrane of claim 7, wherein the carbon molecular sieve membrane has a propylene permeance greater than 20.

9. The carbon molecular sieve membrane of claim 8, wherein the carbon molecular sieve membrane has a propylene permeance greater than 25.

10. The carbon molecular sieve membrane of claim 7, wherein the carbon molecular sieve membrane has a selectivity of at least 10 when separating hydrogen from another gas selected from at least one of ethylene, ethane, propylene, propane, butylene, butane, methane, carbon dioxide, oxygen, nitrogen, and hydrogen sulfide.

11. The carbon molecular sieve membrane of claim 7, wherein the carbon molecular sieve membrane has an asymmetric structure.

12. The carbon molecular sieve membrane of claim 11, wherein the carbon molecular sieve membrane is an asymmetric hollow carbon fiber.

13. A method for separating gases in a gas feed having a plurality of smaller gas molecules and a plurality of larger gas molecules comprising,
   (i) providing a carbon molecular sieve membrane having a Raman G and D peak, wherein the G peak has a wavenumber of at least 1588cm$^{-1}$ and an intensity ratio of the D to the G peak of at most 1.12 as determined at a Raman excitation wavelength of 532 nm; and
   (ii) flowing the gas feed through said carbon molecular sieve membrane to produce a first stream having an increased concentration of the smaller gas molecules and a second stream having an increased concentration of the other gas molecule.

14. The process of claim 13, wherein the gas feed is comprised of at least two of ethylene, ethane, propylene, propane, methane, butane or butylene.

15. The method of claim 14, wherein the gas feed is comprised of at least two of ethylene, ethane, propylene or propane.

16. The method of claim 1, wherein the precursor polymer contains at least two different moieties selected from 2,4,6 trimethyl-1,3-phenylene diamine (DAM), oxydianaline (ODA), dimethyl-3,7-diaminodiphenyl-thiophene-5,5'-dioxide (DDBT), 3,5-diaminobenzoic acid (DABA), 2.3, 5 , 6-tetramethyl-1,4-phenylene diamine (durene), meta - phenylenediamine (m-PDA) , 2,4-diaminotolune (2,4-DAT), tetramethylmethylenedianaline (TMMDA) , 4,4'—diamino 2,2'-biphenyl disulfonic acid (BDSA), 5,5 '-[2,2,2—trifluoro 1- (trifluoromethyl) ethylidene) -1,3—isobenzofurandion (6FDA), 3,3', 4,4'-biphenyl tetracarboxylic dianhydride (BPDA), pyromellitic dianhydride (PMDA), 1,4,5,8- naphthalene tetracarboxylic dianhydride (NTDA), and benzophenone tetracarboxylic dianhydride (BTDA).

* * * * *